United States Patent
Ramos et al.

(10) Patent No.: US 9,844,418 B2
(45) Date of Patent: Dec. 19, 2017

(54) SYSTEM FOR ENDODONTIC TREATMENT

(75) Inventors: Carlos Alberto Spironelli Ramos, Londrina (BR); Michael Yakoby, Kfar Saba (IL)

(73) Assignee: FORUM ENGINEERING TECHNOLOGIES (96) LTD., Rishon Lezion (IL)

( * ) Notice: Subject to any disclaimer, the term of this patent is extended or adjusted under 35 U.S.C. 154(b) by 954 days.

(21) Appl. No.: 13/260,389

(22) PCT Filed: Mar. 24, 2010

(86) PCT No.: PCT/IL2010/000248
§ 371 (c)(1),
(2), (4) Date: Jan. 25, 2012

(87) PCT Pub. No.: WO2010/109464
PCT Pub. Date: Sep. 30, 2010

(65) Prior Publication Data
US 2012/0122055 A1    May 17, 2012

Related U.S. Application Data

(60) Provisional application No. 61/202,660, filed on Mar. 24, 2009, provisional application No. 61/202,800, filed on Apr. 7, 2009.

(51) Int. Cl.
*A61C 5/02* (2006.01)
*A61C 1/00* (2006.01)
*A61C 5/42* (2017.01)

(52) U.S. Cl.
CPC ............. *A61C 1/003* (2013.01); *A61C 5/42* (2017.02)

(58) Field of Classification Search
CPC .................... A61C 1/003; A61C 5/42
USPC .... 433/102, 165, 81, 224, 215, 216; 606/80; 206/368, 369
See application file for complete search history.

(56) References Cited

U.S. PATENT DOCUMENTS

| | | | |
|---|---|---|---|
| 5,944,523 A | 8/1999 | Badoz | |
| 6,293,795 B1 | 9/2001 | Johnson | |
| 2002/0064756 A1 | 5/2002 | Pagnini et al. | |
| 2005/0042572 A1 | 2/2005 | Katsuda et al. | |
| 2009/0136896 A1* | 5/2009 | Meyer Shuster | 433/102 |
| 2010/0040994 A1* | 2/2010 | Johnson | 433/132 |

FOREIGN PATENT DOCUMENTS

| | | |
|---|---|---|
| WO | 0103601 A | 1/2001 |
| WO | 2007085966 A | 8/2007 |

OTHER PUBLICATIONS

Int.'l Searching Authority, PCT International Search Report and Written Opinion (dated Jan. 26, 2011).

* cited by examiner

*Primary Examiner* — Yogesh Patel
(74) *Attorney, Agent, or Firm* — Nath, Goldberg & Meyer; Joshua B. Goldberg; Scott H. Blackman

(57) ABSTRACT

Provided is a system for endodontic treatment of a root canal. The system includes a handpiece containing a rotary motor adapted to rotate an endodontic file secured by the handpiece. A control unit executes a regime of motion of the motor to produce a regime of file motion in which episodes of oscillation of the file are separated by a rotation of the file. When the arc of a rotation is less than the arc of the oscillation that preceded the rotation, the arcs of the episodes of oscillation overlap and the formation of ridges in the root canal is avoided.

11 Claims, 4 Drawing Sheets

(a)   $\alpha_1 = 60°; \beta_1 = 60°$ (b)

$\alpha_2 = 90°; \beta_2 = 90°$ (c)

$\alpha_3 = 120°; \beta_3 = 120°$ (d)

$\alpha_4 = 180°; \beta_4 = 180°$ (e)   $\alpha_4 = 360°$

SYSTEM FOR ENDODONTIC TREATMENT

This is a National Phase Application filed under 35 U.S.C. §371 as a national stage of PCT/IL2010/000248, filed on Mar. 24, 2010, an application claiming the benefit under 35 U.S.C. §119(e) of U.S. Provisional Application No. 61/202,660, filed on Mar. 24, 2009, and an application claiming the benefit under 35 U.S.C. §119(e) of U.S. Provisional Application No. 61/202,800, filed on Apr. 7, 2009, the content of each of which is hereby incorporated by reference in its entirety.

FIELD OF THE INVENTION

This invention relates to systems for endodontic treatment.

BACKGROUND OF THE INVENTION

Endodontic procedures require cleaning of the root canals and canal shaping. Proper cleaning and shaping of the root canals is a crucial factor determining the success of the treatment. In shaping a canal, it is important that the canal wall be smooth and free of "ledges". Cleaning and shaping of the root canal can be done manually using an endodontic file. Usually several endodontic files of different shapes and/or sizes are required to complete the procedure. Motor driven endodontic files (rotary files) are also known. Rotary files are typically tapered and have one or several helical fluted blades. The usage of rotary files was initially limited to straight canals because the stainless steel files were not flexible enough to withstand rotation in curved canals. This situation changed with the development of endodontic files made from Nitinol which have a flexibility about 6 times higher than that of stainless steel files. Nitinol files can withstand motor driven rotary operation even in curved canals.

Nonetheless the Nitinol rotary files are subjected to significant mechanical stress, and after prolonged use, material fatigue can cause sudden breakage of the file without any prior visible deterioration of the file surface. Nitinol files have also been known to become jammed inside the canal and broken by excess torque applied by the motor. This has lead to the development of dental motors intended for endodontic treatments ("endomotors") having a low rotational speed (usually 300 rpm to 1,000 rpm) and low torque (typically up to 6 Ncm) with torque control, enabling stopping or reversing the file rotation when a preset torque limit is reached. Another problem associated with motor driven files is self-threading of the rotating file into the canal due to the helical blades on the file surface. The self-threading effect reduces the dentist's ability to control axial advance of the file and may lead to over-instrumentation.

Dental motors with special reciprocating handpieces which generate a rotary oscillation (reciprocation) of the file with a predetermined arc have also been used. The reciprocating handpieces tend to reduce file breakage caused by jammed files since deformation of the file remains within the resiliency limits of the Nitinol. The oscillating motion prevents self threading and improves control of the axial movement of the file. The arc of oscillation (usually 60° to 90°) tends, however, to cause unequal shaping of the canal walls and to create vertical ledges in the canal wall, which impairs the outcome of the treatment. FIG. 2 shows a cross-section of a tooth root 30 in which ledges 31 have formed due to unequal shaping of the canal wall 32.

U.S. Pat. No. 5,944,523 discloses a motor assembly for root canal treatment and other dental applications based on a stepping motor that generates various movements of the file such as a continuous clockwise or counterclockwise rotation, alternating movement and vibration with low angular amplitude.

To achieve alternating movement of the endodontic file with an appropriate rotational speed (several hundred RPM) fast acceleration and deceleration are required. A stepping motor, on the other hand, is only capable of generating a slow acceleration and deceleration. Furthermore, an alternating movement cannot provide full coverage of the root canal wall and will generate ledges.

U.S. Pat. No. 6,293,795 discloses a device in which clockwise rotation of the endodontic file of a relatively large arc alternates with counterclockwise rotation of a smaller arc. In this way, the cutting edges of the file pass over the entire surface of the root canal providing complete coverage of the canal surface and the creation of vertical ledges is prevented. The alternating movement of the file helps to prevent file breakage and to reduce self threading, which is not completely eliminated since the forward arc of file rotation is always larger than the reverse arc.

Root canals have different cross-section shapes which may be divided in two categories: "round" canals and "flat" canals. FIG. 3 shows the cross section of three roots 35, 36 37 having root canals 40, 41 and 42, respectively, that are essentially round in shape. FIG. 3 also shows the cross section of three roots 34, 38 39 having root canals 43, 44 and 45, respectively, that are essentially flat in shape. The broken circles in FIG. 3 show the cross section of the area cut by an endodontic file in relation to the various root canals. It is important that during root canal cleaning and shaping the maximum surface of the root canal walls be covered. Shaping of a "round" canal is relatively simple since endodontic files with different diameters are manufactured and a file or succession of files optimally suiting a specific "round" canal may be selected for treatment. In case of "flat" canals, the situation is more complicated. The round cross-section of the area cut by an endodontic file does not conform well to the elongated cross-sectional shape of the canal leaving large areas of the canal walls untreated. It is possible to "drive" the file along the flat surface of the canal wall so that the cutting edge of the file "shaves" the wall, but control of such movement is very difficult due to self-threading of the file. Moreover, such poorly controlled movement may easily cause jamming and breakage of the file.

SUMMARY OF THE INVENTION

In one of its aspects, the present invention provides a system for endodontic treatment. The system of the invention a handpiece configured to secure an endodontic file that is rotated by a motor. A control unit having a microprocessor controls the motor in order to execute a predetermined or selectable regime of motion of the file. In one embodiment, the regime of motion comprises the following stages:
  (a) for k=1 to n, where n is an integer;
  (i) oscillating the file from an angular position $\theta_k$ through an arc $\alpha_k$ at a frequency of oscillation $f_k$ for an amount of time $T_k$ or a number of oscillation cycles $M_k$; and
  (ii) rotating the file either clockwise or counterclockwise through an arc $\beta_k$.

In another embodiment of the invention, the microprocessor is configured to execute a regime of motion comprising the following stages:

(i) rotating the file from an angular position $\theta_k$ through an arc $\alpha_k$ at a angular speed $\omega_k$; and
(ii) rotating the file in an opposite direction through an arc $\beta_k$ wherein at least one of the sequences $\{\alpha_k, k=1 \text{ to } n\}$, and $\{\beta_k, k=1 \text{ to } n\}$ includes at least two terms of different values.

The inventors have found that with a regime of file movement in accordance with the invention, material fatigue of the file is reduced. A counter clockwise rotation between oscillations and/or reciprocation motions has been found to reduce the self-threading of the file allowing more precise control of axial file movement. Additionally it was found that file operation according to the invention enables improved control of lateral file movement providing safe means for "shaving" of flat areas of a canal wall. In this mode of operation, the risk of file jamming and breakage during shaving is greatly reduced.

An unexpected benefit of the invention is low level of apical extrusion. During root canal shaping, the debris material should be removed from the canal towards the coronal part. However, some of the debris containing necrotic and contaminated tissues may be extruded through the apical foramen towards the periapical tissues (apical extrusion) causing post-treatment complications. Root canal shaping with rotary instruments used in a rotation mode causes relatively low apical extrusion, while the apical extrusion using reciprocating techniques known in the art is significantly higher. It was found that operation of a rotary file according to the invention causes apical extrusion comparable with that of regular rotary operation and much lower than the apical extrusion of other reciprocation techniques.

Thus, in its first aspect, the invention provides a system for endodontic treatment comprising:
(a) a handpiece containing a rotary motor adapted to rotate an endodontic file secured by the handpiece;
(b) a processor configured to execute a regime of motion of the motor or produce a regime of file motion comprising:
(c) for k=1 to n, where n is an integer;
  (i) oscillating the file from an angular position $\theta_k$ through an arc $\alpha_k$ at a frequency of oscillation $f_k$ for an amount of time $T_k$ or a number of oscillation cycles $M_k$; and
  (ii) rotating the file either clockwise or counterclockwise through an arc $\beta_k$.

The system according to Claim 1 further comprising rotating the file in a continuous clockwise or counterclockwise rotation after completing one or more steps (c).

$\beta_k$ may be less than $\alpha_k$ for at least one k. $\alpha_k$ may be selected from 60°, 90°, 120°, 180°, and 360°. $M_k$ may be in the range of 1 to 10. An angular velocity of the file during an episode of oscillation may be in the range of 300°/sec to 2400°/sec. Any one or more of $\theta_k$, $\alpha_k$, $f_k$, $\beta_k$, $T_k$ and $M_k$ may be predetermined constants for all k, or any one or more of $\theta_k$, $\alpha_k$, $f_k$, $\beta_k$, $T_k$ and $M_k$ may be modulated. The modulation of any one or more of $\theta_k$, $\alpha_k$, $f_k$, $\beta_k$, $T_k$ and $M_k$ may be predetermined, or any one or more of $\theta_k$, $\alpha_k$, $f_k$, $\beta_k$, $T_k$ and $M_k$ may be modulated randomly. Modulation of any one or more of $\theta_k$, $\alpha_k$, $f_k$, $\beta_k$, $T_k$ and $M_k$ may be modulated by a feedback mechanism involving any one or more of a torque exerted on the file, depth of file penetration into a canal, file tip position relative to a canal apex, motor temperature, and elapsed time of treatment.

In another of its aspects, the invention provides a system for endodontic treatment comprising:
(a) a handpiece containing a rotary motor adapted to rotate an endodontic file secured by the handpiece;
(b) a processor configured to execute a regime of motion of the motor or produce a regime of file motion comprising:
(c) for k=1 to n, where n is an integer;
  (i) rotating the file from an angular position $\theta_k$ through an arc $\alpha_k$ at a angular speed $\omega_k$; and
  (ii) rotating the file in an opposite direction through an arc $\beta_k$ wherein at least one of the sets $\{\alpha_k \text{ for } k=1 \text{ to } n\}$, and $\{\beta_k \text{ for } k=1 \text{ to } n\}$ includes at least two terms of different values.

The regime of motion may further comprise rotating the file in a continuous clockwise or counterclockwise rotation after completing one or more steps (c). The $\beta_k$ may be less than $\alpha_k$ for at least one k.

The system according to any one of Claims 12 to 14 wherein $\alpha k$ is selected from 60°, 90°, 120°, 180°, and 360°. An angular velocity of the file during an episode of rotation may be in the range of 300°/sec to 2400°/sec. Any one or more of $\theta_k$, $\alpha_k$, $\omega_k$, and $\beta_k$ are predetermined constants for all k. Any one or more of $\theta_k$, $\alpha_k$, $\omega_k$, and $\beta_k$ may be modulated. The modulation of any one or more of $\theta_k$, $\alpha_k$, $\omega_k$, and $\beta_k$ may be predetermined, or any one or more of $\theta_k$, $\alpha_k$, $\omega_k$, and $\beta_k$ may be modulated randomly. The modulation of any one or more of $\theta_k$, $\alpha_k$, $\omega_k$, and $\beta_k$ may be modulated by a feedback mechanism involving any one or more of a torque exerted on the file, depth of file penetration into a canal, file tip position relative to a canal apex, motor temperature, and elapsed time of treatment.

In another of its aspects, the invention provides a method for operating an endodontic treatment system comprising a file, the method comprising:
(a) for k=1 to n, where n is an integer;
  (i) oscillating the file from an angular position $\theta_k$ through an arc $\alpha_k$ at a frequency of oscillation $f_k$ for an amount of time $T_k$ or a number of oscillation cycles $M_k$; and
  (ii) rotating the file either clockwise or counterclockwise through an arc $\beta_k$.

The method may further comprise rotating the file in a continuous clockwise or counterclockwise rotation after completing one or more steps (a). The $\beta k$ may be less than $\alpha_k$ for at least one k. $\alpha_k$ may be selected from 60°, 90°, 120°, 180°, and 360°. The number of oscillation cycles $M_k$ may be in the range of 1 to 10. An angular velocity of the file during an episode of oscillation may be in the range of 300°/sec to 2400°/sec. Any one or more of $\theta_k$, $\alpha_k$, $f_k$, $\beta_k$, $T_k$ and $M_k$ are predetermined constants for all k. Any one or more of $\theta k$, $\alpha k$, $fk$, $\beta k$, $Tk$ and $Mk$ may be modulated. The modulation of any one or more of $\theta_k$, $\alpha_k$, $f_k$, $\beta_k$, $T_k$ and $M_k$ may be predetermined, or any one or more of $\theta_k$, $\alpha_k$, $f_k$, $\beta_k$, $T_k$ and $M_k$ may be modulated randomly. Modulation of any one or more of $\theta_k$, $\alpha_k$, $f_k$, $\beta_k$, $T_k$ and $M_k$ may be modulated by a feedback mechanism involving any one or more of a torque exerted on the file, depth of file penetration into a canal, file tip position relative to a canal apex, motor temperature, and elapsed time of treatment.

In yet another of its aspects, the invention provides a method for operating an endodontic treatment system comprising a file, the method comprising:
(a) for k=1 to n, where n is an integer;
  (i) rotating the file from an angular position $\theta_k$ through an arc $\alpha_k$ at a angular speed $\omega_k$; and
  (ii) rotating the file in an opposite direction through an arc $\beta_k$ wherein at least one of the sets $\{\alpha_k \text{ for } k=1 \text{ to } n\}$, and $\{\beta_k \text{ for } k=1 \text{ to } n\}$ includes at least two terms of different values.

The method may further comprise rotating the file in a continuous clockwise or counterclockwise rotation after completing one or more steps (a). The $\beta_k$ may be less than $\alpha_k$ for at least one k. $\alpha_k$ may be selected from 60°, 90°, 120°, 180°, and 360°. An angular velocity of the file during an episode of oscillation may be in the range of 300°/sec to 2400°/sec. Any one or more of $\theta_k$, $\alpha_k$, $\omega_k$, and $\beta_k$ are predetermined constants for all k. Any one or more of $\theta_k$, $\alpha_k$, $\omega_k$, and $\beta_k$, may be modulated. Any one or more of $\theta_k$, $\alpha_k$, $\omega_k$, and $\beta_k$, may be predetermined, or any one or more of $\theta_k$, $\alpha_k$, $\omega_k$, and $\beta_k$ may be modulated randomly. Modulation of any one or more of $\theta_k$, $\alpha_k$, $\omega_k$, and $\beta_k$, may be modulated by a feedback mechanism involving any one or more of a torque exerted on the file, depth of file penetration into a canal, file tip position relative to a canal apex, motor temperature, and elapsed time of treatment.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
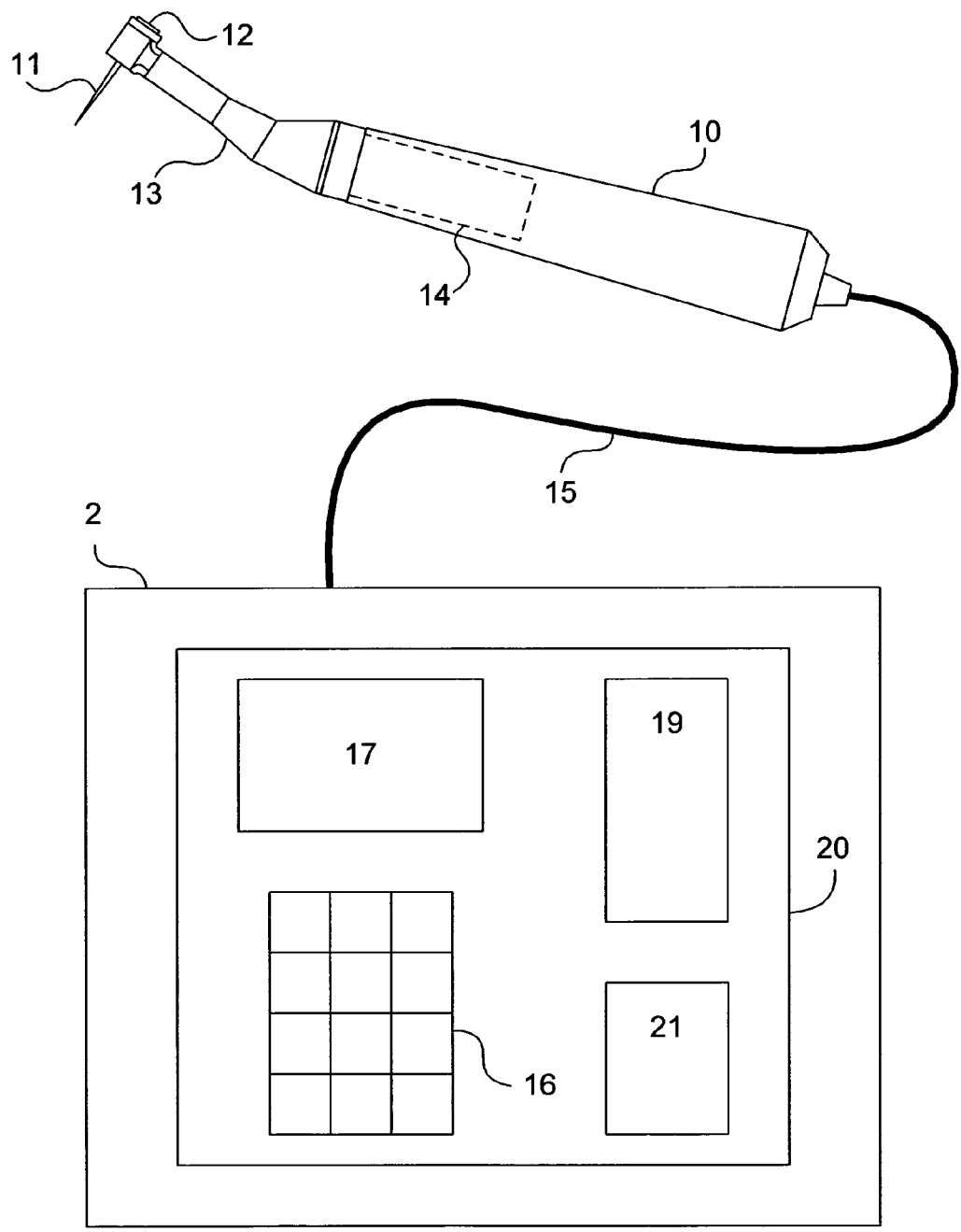
FIG. 1 shows a system of endodontic treatment in accordance with one embodiments of the invention.
Figure 2:
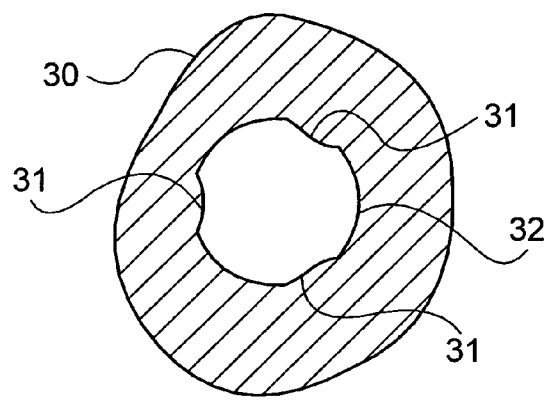
FIG. 2 shows a tooth root and root canal in which ledges have formed.
Figure 3:
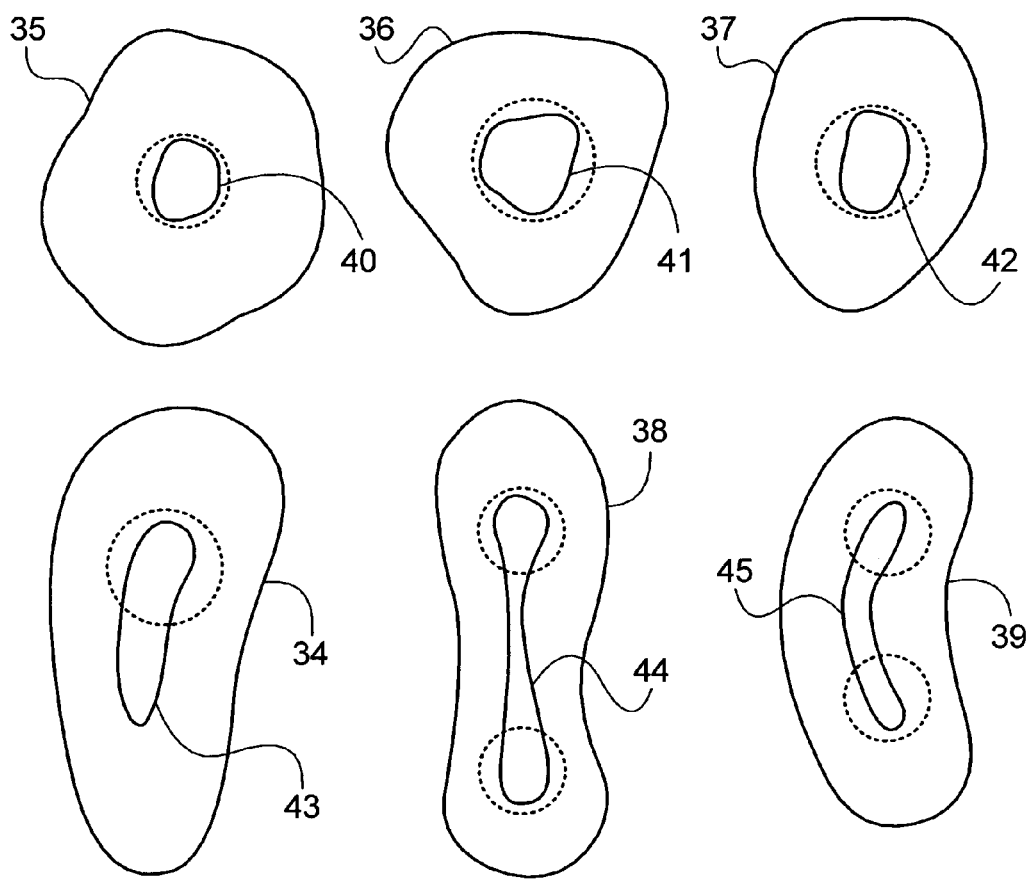
FIG. 3 shows tooth roots having circular and flat root canals.

FIG. 1 shows a system 2 for endodontic treatment in accordance with one embodiment of the invention. The system 2 comprises a handpiece 10 and a control unit 20. An endodontic file 11 is secured in a chuck of the handpiece head 12. The handpiece 10 further comprises an electric motor 14 fastened to a contra angle 13. The motor 14 is connected by a cable 15 to the control unit 20 which includes a microprocessor 19, a memory 21 a keyboard 16 and a display 17. The control system 20 controls the motor 14 in order to execute a predetermined or selectable regime of motion of the file 11, as explained below. In a cordless embodiment, the control unit is incorporated into the handpiece 10 and the system is battery operated. In another embodiment, the control unit is incorporated into the handpiece 10 and the system can alternate between being cordless or connected by a cable 15 to the host control/power source/charger unit.

The memory 21 may be used to store operational parameters, such as speed, torque, operational sequences, etc. of an endodontic treatment; as well as a library of operational parameters for different files and/or file systems. The control unit 20 may include any one or more of a non-volatile memory, wired or wireless communication channels, an Internet channel, data storage media, etc.

In accordance with the invention, the microprocessor 19 is configured to execute a phase controlled regime of motion. In one embodiment, the regime of motion comprises the following stages:

(a) for k=1 to n, where n is an integer;
(i) oscillating the file from an angular position $\theta_k$ through an arc $\alpha_k$ at a frequency of oscillation $f_k$ for an amount of time $T_k$ or a number of oscillation cycles $M_k$; and (ii) rotating the file either clockwise or counterclockwise through an arc $\beta_k$.

Figure 4:
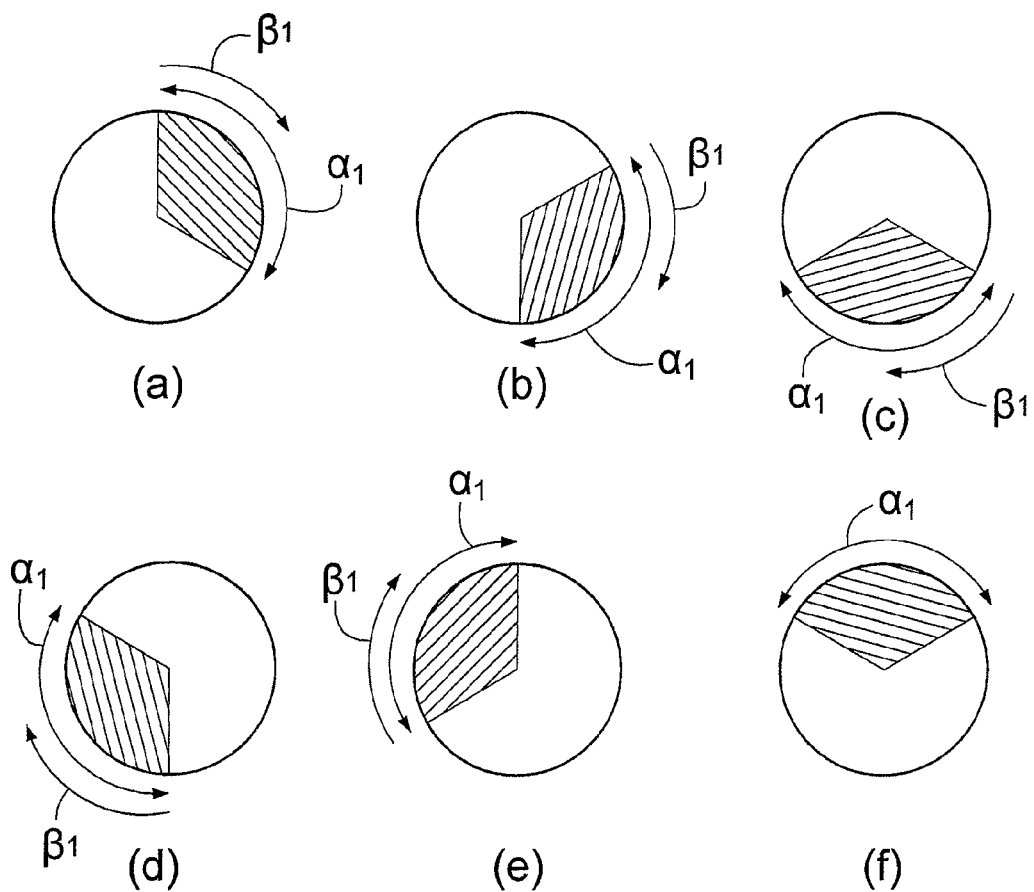
FIG. 4 shows a regime of motion of an endodontic file in accordance with one embodiment of the invention.

FIG. 4 shows schematically an example of the regime of motions according to this embodiment for treating a root canal 50. The regime begins in FIG. 4a with an oscillation of the file in an arc $\alpha_1$=120°. At the termination of $M_1$=10 oscillations, the file is rotated through an arc $\beta_1$=60° and the file is then oscillated through an arc $\alpha_2$=120° at the new location (FIG. 4b) and after $M_2$=10 oscillations rotated through an arc $\beta_2$=60° (FIG. 4c). The process continues with oscillations of $\alpha_3$=120°, $M_3$=5 (FIG. 4c); $\alpha_4$=120°, $M_4$=5 (FIG. 4d); $\alpha_5$=120°, $M_5$=3 (FIG. 4e) and $\alpha_6$=120°, $M_6$=3 (FIG. 4d), interspersed with rotations $\beta_3$=60°, $\beta_4$=60°, and $\beta_5$=60°, as indicated in FIG. 4. Since $\beta_k$ is less than $\alpha_k$ for all k, the arcs of oscillations for different k overlap (six overlapping oscillations of 120° are used to completely cover the entire 360° circumference of the canal), and the formation of ledges is thus avoided. Most endodontic files have more than one cutting edge (usually 2 to 4) and the full coverage of the entire circumference of the canal can be achieved in fewer steps.

Figure 5:
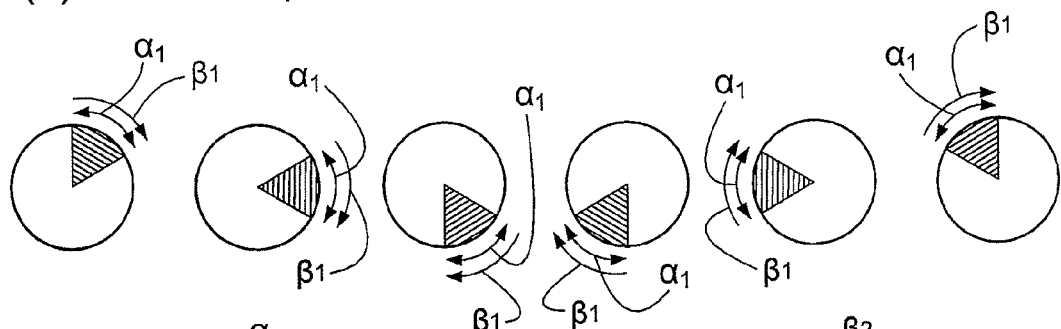
FIG. 5 shows a regime of motion of an endodontic file in accordance with another embodiment of the invention.
Figure 5:
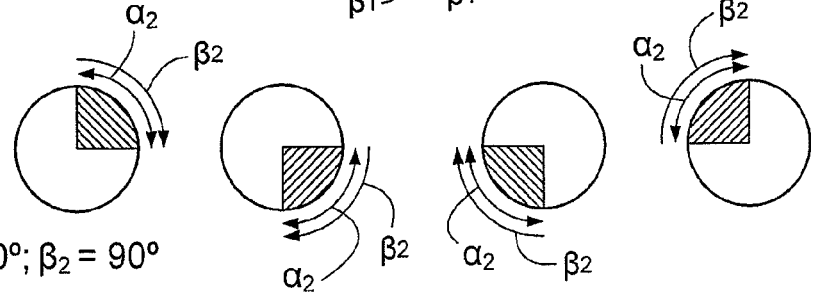
Figure 5:
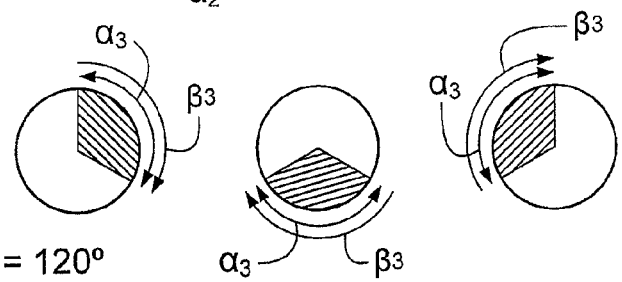
Figure 5:
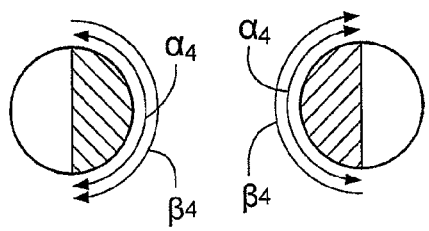
Figure 5:
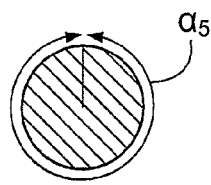

Typically, the number of oscillation cycles $M_k$ is in the range of 1 to 10, and the angular velocity of the file during an oscillation stage is typically in the range of 300°/sec to 2400°/sec. $\beta_k$ may be less than, greater than, or equal to $\alpha_k$. Setting $\beta_k$ less than $\alpha_k$ ensures overlap of the coverage of the canal wall during consecutive oscillation stages. $\alpha_k$ may increase with increasing k. For example, as shown in FIG. 5, a regime may consist of several oscillation stages with $\alpha_k$=60°, $M_k$=10 and $\beta_k$=60° (FIG. 5a) followed by oscillation stages with $\alpha_k$=90°, $M_k$=10 and $\beta_k$=90° (FIG. 5b); then with $\alpha_k$=120°, $M_k$=10 and $\beta_k$=120° (FIG. 5c); $\alpha_k$=180°, $M_k$=10 and $\beta_k$=120° (FIG. 5d) and with $\alpha_k$=360°, $M_k$=10 (FIG. 5e). The regime of motion may further comprise rotating the file in a continuous clockwise or counterclockwise rotation after completing the reciprocation stages.

Any one or more of $\theta_k$, $\alpha_k$, $f_k$, $\beta_k$, $T_k$ and $M_k$ may be predetermined constants for all k. or any one or more of $\theta_k$, $\alpha_k$, $f_k$, $\beta_k$, $T_k$ and $M_k$ may be modulated. The modulation may be predetermined or random. The modulation may be determined during use by a feedback mechanism involving, for example, any one or more of a torque exerted on the file, depth of file penetration into a canal, file tip position relative to a canal apex, motor temperature, and elapsed time of treatment.

As an example, in a preferred embodiment, when the torque applied to the file exceeds a predefined value, any one or more of the arcs, frequency or duration/number of oscillations can be modulated. For instance, the oscillation arc ($\alpha_k$) and/or the oscillation frequency can be reduced and/or the number of oscillations ($M_k$) or the duration of oscillations ($T_k$) can be increased. As another example, in preferred embodiment, when the file tip is advanced to a predetermined position relative to the apex, any one or more of the oscillation/reciprocation arcs, frequency or duration/number of cycles can be modulated, the motor may be stopped or reverse rotation can be activated, etc. For instance, when the file tip has reached the apical position, the oscillation/reciprocation frequency and the arcs may be reduced; audio feedback may be activated, etc.

In another embodiment of the invention, the microprocessor 19 is configured to execute a regime of motion comprising the following stages:

(i) rotating the file from an angular position $\theta_k$ through an arc $\alpha_k$ at a angular speed $\omega_4$; and (ii) rotating the file in an opposite direction through an arc $\beta_k$ wherein at least one of the sequences $\{\alpha_k, k=1 \text{ to } n\}$ and $\{\beta_k, k=1 \text{ to } n\}$ includes at least two terms of different values.

In a different embodiment the system may be combined with additional dental devices, such as apex locator, vitality tester, file identification system, file working length measurement system, file selection system, gutta-percha cutter, gutta-percha condenser, photo-polymerization lamp, trans-illumination lamp and others.

The invention claimed is:

1. A system for endodontic treatment, comprising:
    (a) a handpiece containing a rotary motor adapted to rotate an endodontic file secured by the handpiece;
    (b) a processor configured to execute a regime of motion of the motor or produce a regime of file motion comprising:
    (c) for k=1 to n, where n is an integer;
        (i) oscillating the file through an arc $\alpha_k$ at a frequency of oscillation $f_k$ for an amount of time $T_k$ or a number of oscillation cycles $M_k$; and
        (ii) rotating the file either clockwise or counterclockwise through an arc $\beta_k$.

2. The system according to claim 1, further comprising rotating the file in a continuous clockwise or counterclockwise rotation after completing one or more steps (c).

3. The system according to claim 1, wherein the $\beta_k$ is less than $\alpha_k$ for at least one k.

4. The system according to claim 1, wherein $\alpha_k$ is selected from the group consisting of 60°, 90°, 120°, 180°, and 360°.

5. The system according to claim 1, wherein the number of oscillation cycles $M_k$ is in the range of from 1 to 10.

6. The system according to claim 1, wherein an angular velocity of the file during an episode of oscillation is in the range of from 300°/sec to 2400°/sec.

7. The system according to claim 1, wherein any one or more of $\alpha_k$, $f_k$, $\beta_k$, $T_k$, and $M_k$, are predetermined constants for all k.

8. The system according to claim 1, wherein any one or more of $\alpha_k$, $f_k$, $\beta_k$, $T_k$, and $M_k$, are modulated.

9. The system according to claim 8, wherein modulation of any one or more of $\alpha_k$, $f_k$, $\beta_k$, $T_k$, and $M_k$, is predetermined.

10. The system according to claim 8, wherein modulation of any one or more of $\alpha_k$, $f_k$, $\beta_k$, $T_k$, and $M_k$, are modulated by a feedback mechanism comprising any one or more of a torque exerted on the file, depth of file penetration into a canal, file tip position relative to a canal apex, motor temperature, and elapsed time of treatment.

11. The system according to claim 8, wherein any one or more of $\alpha_k$, $f_k$, $\beta_k$, $T_k$, and $M_k$, are modulated randomly.

* * * * *